United States Patent [19]
Torvinen

[11] Patent Number: 6,159,130
[45] Date of Patent: Dec. 12, 2000

[54] MEASURING METHOD AND MEASURING SYSTEM

[75] Inventor: Vesa-Pekka Torvinen, Oulu, Finland

[73] Assignee: Polar Electro Oy, Kempele, Finland

[21] Appl. No.: 09/315,095

[22] Filed: May 19, 1999

[30] Foreign Application Priority Data

May 20, 1998 [FI] Finland ..................................... 981133

[51] Int. Cl.$^7$ ................................................ A63B 21/005
[52] U.S. Cl. ................................ 482/8; 482/57; 482/901; 73/379.01
[58] Field of Search .............................. 482/1–9, 51, 54, 482/57, 900–902; 600/587, 595; 607/77; 73/379.01, 379.07

[56] References Cited

U.S. PATENT DOCUMENTS 6,033,344  3/2000  Trulaske et al. ............................ 482/7

FOREIGN PATENT DOCUMENTS 100924  3/1998  Finland .

Primary Examiner—Glenn E. Richman
Attorney, Agent, or Firm—Hoffmann & Baron, LLP

[57] ABSTRACT

The invention relates to a measuring method and a measuring system, particularly suited for measuring the function of at least one organ of a user non-invasively. The system comprises a transmitter unit (200) attached to the user's body, and a receiver unit (202). The transmitter unit (200) transfers its measurement data associated with at least one organ to the receiver unit (202), and at least one sensor (208, 210 to 214) measures other properties than the function of the user's organs when the user uses an exercise device. The measuring system includes a holder (206) having a data collection unit (204). The receiver unit (202) is secured to the holder (206), and at least one said sensor (208, 210 to 214) transfers its measurement data to the data collection unit (204). The data collection unit (204) transfers the collected measurement data to the receiver unit (202) by means of inductive interaction.

28 Claims, 2 Drawing Sheets

MEASURING METHOD AND MEASURING SYSTEM

FIELD OF THE INVENTION

The invention relates to a measuring method suitable particularly for system which measures the function of at least one organ of a user non-invasively, and comprises a transmitter unit which is attached to the user's body, and a receiver unit. The transmitter unit transfers its measurement data associated with at least one organ or organs to the receiver unit, and at least one sensor measures additional properties other than the function of the user's organs when the user uses an exercise device.

The invention further relates to a measuring system which measures particularly the function of at least one organ of a user non-invasively, and comprises a transmitter unit attached to the user's body, and a receiver. The receiver is arranged to transfer its measurement data associated with at least one organ to the receiver unit, and least one sensor is arranged to measure additional properties other than the function of the user's organs when the user uses an exercise device.

BACKGROUND OF THE INVENTION

Telemetric measuring methods are, for instance, used for measuring a person's heart rate. Equipment solutions are usually such that the unit for measuring and transmitting the heart rate data is arranged around the person's chest as a transmitter belt, from which the measurement data is telemetrically transferred by means of inductive coupling to a receiver unit, often implemented as a receiver wristband on a person's wrist. In cycling, the receiver unit can be secured to a bicycle handlebar, for example.

The transmitters of heart rate measurement devices transmit a burst of approximately 5 kHz each time the transmitters detect an ECG signal. The transmitter circuit of the transmitter unit comprises a resonance unit of a coil and a capacitor, the resonance circuit being activated and controlled by the heart rate. The receiver unit computes the pulse frequency on the basis of the time difference between successive transmitted signals, i.e. the time difference of the bursts, the information to be transmitted, i.e. the heart rate, being thus included in the transmission coded in the interval between the pulses.

Currently, however, a need has arisen for telemetric transmission of measurement data from several different sensors, for instance heart rate, pedaling speed and pedaling cadence, to the same receiver. In the prior art, the sensors transmit a measurement signal as a pulse group. In a pulse group, three pulses form two intervals which differ from the intervals of the pulse groups of other variables. Such a 3-pulse-coding is called a 3-pulse transmission. The receiver unit identifies each measurement variable on the basis of the pulse group interval.

Many applications, however, require higher-rate data transfer than the 3-pulse transmission is able to offer. In addition, the receiver unit is only capable of distinguishing a limited number of sensors from each other due to the coding employed in the 3-pulse transmission.

BRIEF DESCRIPTION OF THE INVENTION

An object of the invention is thus to provide a method and an apparatus implementing the method such that the above problems can be solved. This is achieved with a method of the type described in the introduction, the method being characterized in that the measuring system comprises a holder comprising a data collection unit, and a receiver is secured to the holder. At least one sensor transfers its measurement data to the data collection unit of the holder; and the data collection unit of the holder transfers the collected measurement data to the receiver unit by means of inductive interaction.

The system of the invention is characterized in that the measuring system comprises a holder further comprising a data collection unit, and a receiver unit is arranged to be secured to the holder. At least one sensor is arranged to transfer the collected measurement data to the receiver unit by means of inductive interaction.

Several advantages are achieved with the method and system of the invention. Data transfer rate to the receiver unit can be increased. Transmission power necessary for data transfer can be decreased, and the measuring system of the invention is more efficient in data processing than the prior art.

BRIEF DESCRIPTION OF THE DRAWINGS

The invention is now described in greater detail in connection with the preferred embodiments with reference to the accompanying drawings, in which.

DETAILED DESCRIPTION OF THE INVENTION

The solution of the invention can be applied when at least two different measurement variables are provided, but it can be particularly applied to cycling, where the measurement variables include the cyclist's heart rate, speed of the cycle, pedaling cadence and/or other characteristics of the user or the environment.

Figure 1:
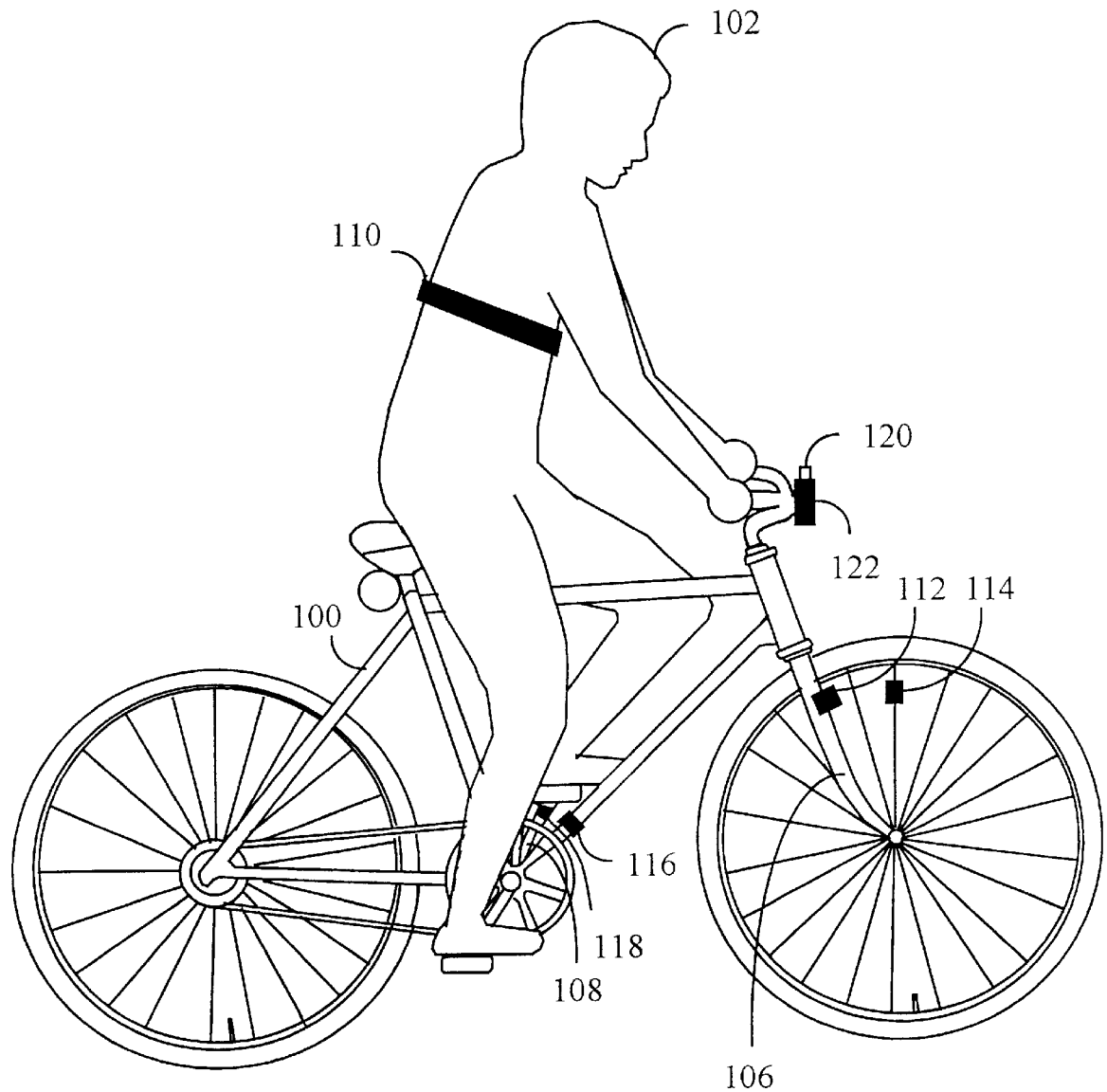
FIG. 1 shows a prior art measuring system.

FIG. 1 shows three transmitter units used in a prior art method and a receiver unit in a cycling environment. The application is, for instance, a bicycle 100, pedaled by a user 102. The apparatus comprises for example three measuring and transmitter units 110 to 116, one receiver unit 120 to which each measuring and transmitter unit telemetrically transfers measurement data as pulse groups, and a holder 122 of the receiver.

In FIG. 1, a first measuring and transmitter unit 110, i.e. a heart rate transmitter, is provided for measuring and transmitting the heart rate. The first measuring and transmitter unit 110 comprises an ECG sensor (an ECG amplifier), a control block and an oscillating resonance circuit controlled by heart rate. The oscillating resonance circuit comprises a coil and a capacitor, coupled in parallel (not shown in the figure). Hence, the heart beat data is transferred to the receiver 120 by means of inductive interaction, since the receiver 120 also comprises the oscillating circuit formed by a coil and a capacitor.

In FIG. 1, a second measuring and transmitter unit 112, i.e. a speed transmitter, is provided for measuring the speed of an exercise device. The second measuring and transmitter unit 112 comprises a speed sensor, a control block and an oscillating resonance circuit controlled by a speed signal. The oscillating resonance circuit comprises a coil and a capacitance, coupled in parallel (not shown in the figure) .The speed sensor can be implemented, for instance, by a magnetic switch sensor such that a magnet 114 is secured to a wheel 104 of the bicycle 100, and the switch part of the magnet is in its place on a front fork 106 of the bicycle. The case the speed measurement is based on detecting the movement of the magnet past the switch part. In a preferred embodiment, the speed sensor 112 further comprises for instance a ¼ divider, which makes the sensor issue a pulse only after the magnet has revolved four times past the switch part. In this way, by using the divider, high speeds can be measured, whereas lower speeds can be measured without the divider being utilized.

In FIG. 1, a third measuring and transmitter unit 116, i.e. a cadence transmitter (a transmitter indicating the pedaling cadence) provided for measuring the pedaling cadence of the user 102 of the exercise device, i.e. the person pedaling. The third measuring and transmitter unit 116 comprises a cadence sensor, a control unit, an amplifier and an oscillating resonance circuit controlled by a cadence signal. The oscillating resonance circuit comprises a coil and a capacitance, which is coupled in parallel (not shown in the figure). The cadence sensor can be implemented by a magnetic switch sensor such that a magnet 118 is secured to a pedal of the bicycle 100 or to a crank 108 of the pedals. The switch part of the sensor and the actual transmitter unit are secured, for instance, to the frame tube of the bicycle 100, in which case the measurement of the pedaling cadence is based on detecting the movement of the magnet past the switch part of the sensor. In such a prior art solution, the receiver 120 directly receives the measurement signals transmitted by the sensors 112, 116, and the holder 122 only serves as a mechanical securing means of the receiver unit 120 to the exercise device.

Figure 2:
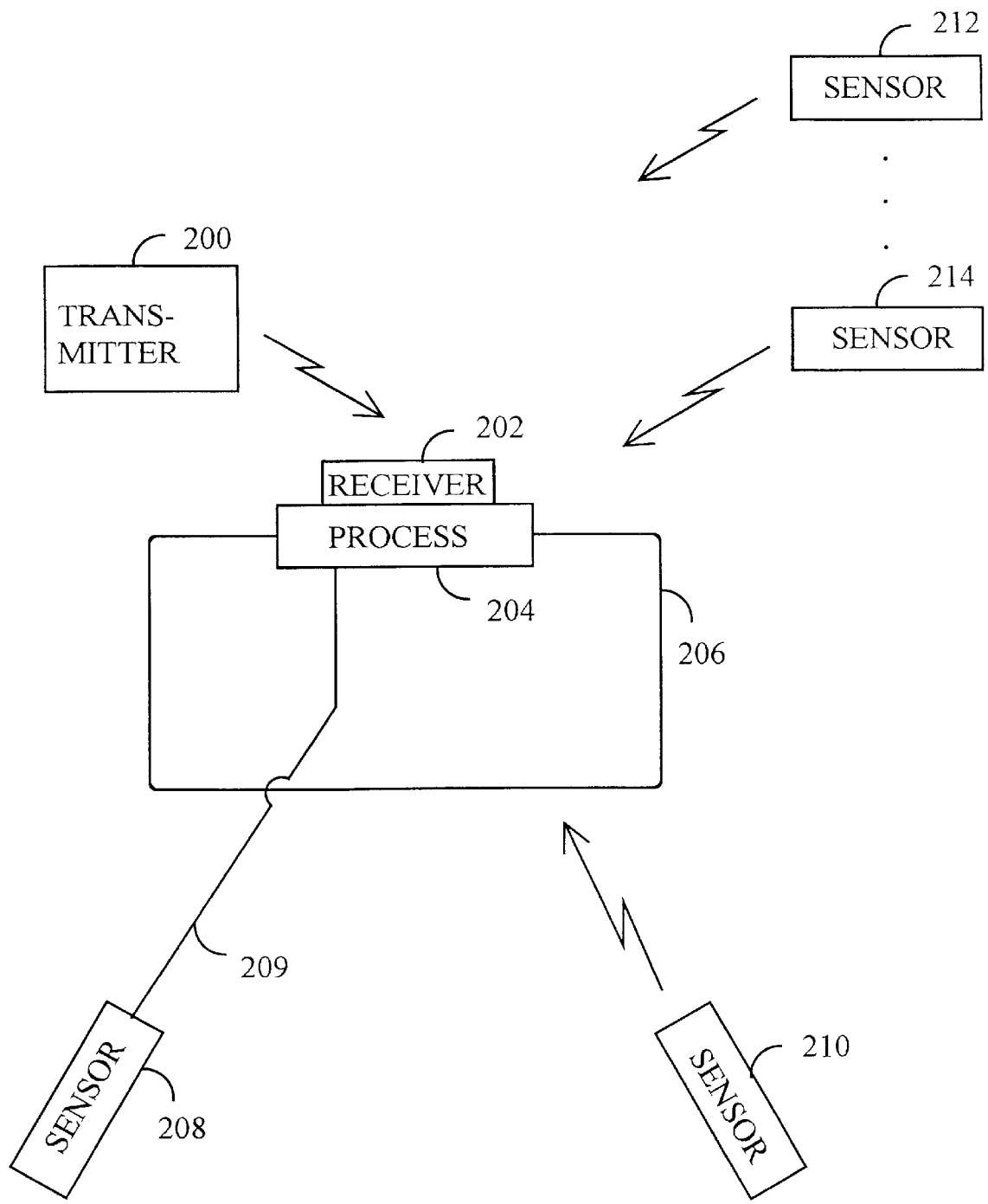
FIG. 2 shows a measuring system formed in accordance with the invention.

FIG. 2 shows a measuring system in accordance with the inventive solution. Superficially, the measuring system of the invention may seem to be similar to the prior art solution, but the operation potential of the system of the invention is substantially greater than that of the prior art solution. The system comprises a holder 206 secured to, exercise device, the holder comprising a data collection unit 204. The holder 206 with its data collection unit 204 is substantially different from the prior art and enables much more efficient data transfer and data processing. The holder 206, in accordance with FIG. 2 and the holder in FIG. 1, are thus secured to the bicycle in a similar manner. The difference is the functional activity of the holder 206, which is enabled by the data collection unit 204. Sensors 208, 210, 212, 214 transmit their measurement data to the data collection unit 204. Data transfer between the sensors 208, 210, 212, 214 and the data collection unit 204 can take place through a wire. In FIG. 2, this is illustrated by a wire 209, which combines the sensor 208 and the data collection unit 204. Data transfer can also take place wirelessly. In this case, the data transfer of the sensor 210 to the data collection unit 204 takes place by means of inductive interaction. The actual mode of data transfer is not essential in the inventive solution, but the fact that the data collection unit 204 collects the measurement data transmitted by the sensors 208, 210, 212, 214 is important. The data collection unit 204 can also change the coding of the measurement data received and transfer the measurement data to the receiver unit at a substantially higher data transfer rate than the data transfer rate between the sensor or sensors and the data collection unit 204. The data collection unit 204 preferably processes the measurement data received. Consequently, the data collection unit 204 can for instance compute the speed of the exercise device from the pulses received from the speed sensor, and instead of transmitting the pulses from the sensor further to the receiver unit 202, the data collection unit 202 can transmit the computed speed information. In the prior art, the signal of a sensor can only be comprised of, for instance, pulses of the 3-pulse transmission that are generated when the magnet passes the switch part, as mentioned in the description of FIG. 1. In the inventive solution, information on which or what kind of sensor the measurement data originates from is transmitted together with the measurement data of each sensor 208, 210 to 214. Hence, the measurement data of the sensors 208, 210 to 214 can be separated from each other. It is also ensured that the measurement data from the different sensors 208, 210 to 214 is not mixed up when transferred between the data collection unit 204 and the receiver unit 202.

In the inventive solution, the data collection unit 204 can form a new performance parameter from measurement data received from one sensor. When, for example, the speed of the bicycle is measured by the speed sensor, the data collection unit computes from the speed data received for the new performance parameter statistical variables such as speed change, speed mean value or speed deviation. The performance parameter is transferred to the receiver unit in accordance with the inventive solution. The user can thus analyze and modify his or her exercise technique.

The inventive solution also enables measurement data issued from two or more sensors to be combined into a new performance parameter. For example, cadence data and speed data, or data from other sensors can be combined into a performance parameter in such a manner that instantaneous or statistical cadence and speed data are compared with each other. The ratio between the cadence and the speed thus formed is preferably transferred to the data collection unit 204.

The inventive solution also allows heart rate transmitted by the transmitter 200 to be directly received by the data collection unit 204. The data collection unit 204 transfers the heart rate data to the receiver 202 by means of inductive interaction.

The inventive solution enables the transmitter unit 200 to transmit its measurement data to the data collection unit 204, but in a preferred embodiment of the invention the transmitter unit 200 transfers its measurement data directly to the receiver unit 202 by means of inductive interaction using different modulation and/or coding than in the data transfer between the data collection unit 204 and the receiver unit 202. The data collection unit transfers the measurement data to the receiver unit 202 using a higher data transfer rate than the wireless data transfer rate taking place between the sensors 210 to 214 and the data collection unit 204. This enables the measurement data produced by the sensors 208, 210 to 214 to be transferred to the receiver unit 202 sufficiently fast. The data transfer is preferably performed in serial mode. Serial-mode data transfer is preferably similar to that of the prior art solutions wherein the receiver unit 202 communicates with the data transfer unit. The data collection unit 204 identifies the attachment of the receiver unit 202 to the holder 206. The identification is performed by means of a switch, for example. On the basis of the identification, the data collection unit 204 transmits a handshake signal to the receiver unit 202. The handshake signal can comprise a number of pulses, for example. After receiving the handshake signal, the receiver unit 202 sets its operational mode to be suitable for the exercise device. In connection with the exercise device, the receiver unit 202 receives data measured by the sensors 208, 210 to 214 by means of the data collection unit 204.

The sensor or sensors 208, 210 to 214 transfer measurement data to the data collection unit at least partly wirelessly.

The sensor 208, 210 to 214 thus transfers its measurement data to the data collection unit 204 preferably by means of inductive interaction. In the measuring system of the invention, the coil (not shown in the figure) of the sensor 208, 210 to 214 participating in the inductive interaction can readily be directed for data transfer to the data collection unit 204. Hence, the transmission power of the sensor 208, 210 to 214 can be kept low. At least one sensor 208, 210 to 214, in accordance with the number of the sensors, measures one or more characteristics, such as the speed of the exercise device, ambient temperature and pressure. Furthermore, when the exercise involves repeating a particular motion, the cadence of the repetitive motion can be measured. The exercise device is preferably a bicycle, in which case at least two sensors 208, 210 to 214 are provided, which measure the speed and pedaling cadence of the bicycle.

The receiver unit comprises at least two modes. The first mode is such that the user does not exercise on the exercise device and the receiver unit 202 is in inductive interaction with, for example, the transmitter unit 200, having no interaction with the data collection unit 204. Such a mode enables the receiver unit 200 to be used in accordance with the prior art when the user is running, for example. The second mode is such that the user exercises on the exercise device and the receiver unit 202 is in inductive interaction with at least the data collection unit 204.

The invention can also be applied to exercise devices other than a bicycle. Such devices include watercraft, in which case the measurement variables include a person's heart rate, speed and operating cadence of a watercraft, such as paddling or rowing cadence. Furthermore, the invention can be applied to an application where a substantial part of the measurement variables or even all measurement variables are measurements related to the human body, such as two or more of the following: heart rate, blood pressure, temperature, blood glucose content and blood oxygen content. The inventive solution also enables the condition of the exercise device to be measured by means of different sensors. In connection with a bicycle, the sensors can measure for example the brakes (brake wear or brake force), gears (gear shift and gear wear), shaking of the bicycle, tightness of the chain or the power used.

Although the invention has been described with reference to the example of the accompanying drawings, it is obvious that the invention is not restricted thereto but can be modified in many ways within the scope of the inventive idea disclosed in the attached claims.

What is claimed is:

1. A method of non-invasively measuring a function of at least one organ of a user, the method adapted for use in a measuring system, the measuring system including at least one sensor, a transmitter unit, and a receiver unit, the at least one sensor collecting measurement data from the at least one organ of the user, the measurement data being representative of the function of the at least one organ of the user, the transmitter unit being attached to the user, the method comprising the steps of:

transferring the measurement data from the at least one sensor to a data collection unit associated with a holder;

processing the measurement data in the data collection unit; and transferring the processed measurement data from the data collection unit to the receiver unit by inductive interaction.

2. A method of non-invasively measuring a function of at least one organ of a user as defined by claim 1, wherein the transmitter unit is responsive to the measurement data, the method further including the steps of:

encoding the measurement data by the transmitter unit using a first technique; and transferring the encoded measurement data from the transmitter unit to the receiver unit by inductive interaction, wherein the step of processing the measurement data in the data collection unit includes the step of encoding the measurement data using a second technique, the second technique being different from the first technique.

3. A method of non-invasively measuring a function of at least one organ of a user as defined by claim 1, wherein the transmitter unit is responsive to the measurement data, the method further including the step of transferring the measurement data from the transmitter unit to the data collection unit.

4. A method of non-invasively measuring a function of at least one organ of a user as defined by claim 1, wherein the step of transferring the processed measurement data from the data collection unit to the receiver unit by inductive interaction includes the step of transferring the measurement data from the data collection unit to the receiver unit serially.

5. A method of non-invasively measuring a function of at least one organ of a user as defined by claim 1, wherein the step of transferring the processed measurement data from the data collection unit to the receiver unit by inductive interaction includes the step of transferring the measurement data from the data collection unit to the receiver unit at least partially wirelessly.

6. A method of non-invasively measuring a function of at least one organ of a user as defined by claim 1, wherein the step of transferring the measurement data from the at least one sensor to the data collection unit includes the step of transferring the measurement data by inductive interaction data from the at least one sensor to the data collection unit.

7. A method of non-invasively measuring a function of at least one organ of a user as defined by claim 1, further including the steps of:

identifying an attachment of the receiver unit to the holder by the data collection unit;

transmitting a handshake signal from the data collection unit to the receiver unit in response to identifying the attachment of the receiver unit to the holder; and setting an operational mode in the receiver unit in response to receiving the handshake signal, the operational mode being associated with exercising.

8. A method of non-invasively measuring a function of at least one organ of a user as defined by claim 1, further including the step of:

selecting at least one of a first mode and a second mode in the receiver unit, the first mode being selected when the user is not exercising, the receiver unit inductively interacting with one of the transmitter unit and the data collection unit in the first mode, the second mode being selected when the user is exercising, the receiver unit inductively interacting with at least one of the transmitter unit and the data collection unit in the second mode.

9. A method of non-invasively measuring a function of at least one organ of a user as defined by claim 1, further including the step of measuring at least one of a speed of an exercise device, an ambient temperature, a pressure, and a cadence by the at least one sensor.

10. A method of non-invasively measuring a function of at least one organ of a user as defined by claim 1, further including the step of measuring at least one property associated with an exercise device by the at least one sensor.

11. A method of non-invasively measuring a function of at least one organ of a user as defined by claim 1, further including the step of measuring at least one of a speed of a bicycle and a pedaling cadence of the bicycle by the at least one sensor.

12. A method of non-invasively measuring a function of at least one organ of a user as defined by claim 1, wherein the step of transferring the processed measurement data from the data collection unit to the receiver unit by inductive interaction is performed at a substantially higher rate than the step of transferring the measurement data from the at least one sensor to the data collection unit.

13. A method of non-invasively measuring a function of at least one organ of a user as defined by claim 1, wherein the step of processing the measurement data in the data collection unit further includes the step of generating a performance parameter from the measurement data.

14. A method of non-invasively measuring a function of at least one organ of a user as defined by claim 1, wherein the step of processing the measurement data in the data collection unit further includes the step of generating at least one statistical variable from the measurement data.

15. A measuring system, the measuring system being able to measure a function of at least one organ of a user, the measuring system comprising:
- at least one sensor, the at least one sensor collecting measurement data from the at least one organ of the user, the measurement data being representative of the function of the at least one organ;
- a transmitter unit, the transmitter unit being attached to the user;
- a receiver unit; and
- a holder, the holder including a data collection unit, the receiver unit being attached to the holder, the at least one sensor transferring measurement data to the data collection unit, the data collection unit performing at least one of processing and encoding the measurement data received from the at least one sensor, the data collection unit being able to transfer the measurement data to the receiver unit by inductive interaction.

16. A measuring system as defined by claim 15, wherein the transmitter unit is responsive to the measurement data, the data collection unit using a first technique of at least one of modulation and encoding to transfer the measurement data to the receiver unit, the transmitter unit using a second technique of at least one of modulation and encoding to transfer the measurement data to the receiver unit, the second technique being different from the first technique.

17. A measuring system as defined by claim 15, wherein the transmitter unit is responsive to the measurement data, the measurement data being transferred from the transmitter unit to the data collection unit.

18. A measuring system as defined by claim 15, wherein the measurement data is transferred from the data collection unit to the receiver unit serially.

19. A measuring system as defined by claim 15, wherein the measurement data is transferred from the data collection unit to the receiver unit at least partially wirelessly.

20. A measuring system as defined by claim 15, wherein the at least one sensor transfers the measurement data to the data collection unit by inductive interaction.

21. A measuring system as defined by claim 15, wherein the data collection unit identifies an attachment of the receiver unit to the holder, the data collection unit transmitting a handshake signal to the receiver unit in response to identifying the attachment of the receiver unit to the holder, the receiver unit being in an operational mode in response to receiving the handshake signal, the operational mode being associated with exercising.

22. A measuring system as defined by claim 15, wherein the receiver unit includes a first mode and a second mode, the first mode being selected when the user is not exercising, the receiver unit inductively interacting with one of the transmitter unit and the data collection unit in the first mode, the second mode being selected when the user is exercising, the receiver unit inductively interacting with at least one of the transmitter unit and the data collection unit in the second mode.

23. A measuring system as defined by claim 15, wherein the at least one sensor measures at least one of a speed of an exercise device, an ambient temperature, a pressure, and a cadence.

24. A measuring system as defined by claim 15, wherein the at least one sensor measures at least one of a speed of a bicycle and a pedaling cadence of the bicycle.

25. A measuring system as defined by claim 15, wherein the at least one sensor measures at least one property associated with an exercise device.

26. A measuring system as defined by claim 15, wherein the measurement data is transferred from the data collection unit to the receive unit by inductive interaction at a substantially higher rate than the measurement data is transferred from the at least one sensor to the data collection unit.

27. A measuring system as defined by claim 15, wherein the data collection unit generates a performance parameter from the measurement data.

28. A measuring system as defined by claim 15, wherein the data collection unit generates at least one statistical variable from the measurement data.

* * * * *

UNITED STATES PATENT AND TRADEMARK OFFICE
CERTIFICATE OF CORRECTION

PATENT NO. : 6,159,130
DATED : December 12, 2000
INVENTOR(S) : Vesa-Pekka Torvinen It is certified that error appears in the above-identified patent and that said Letters Patent is hereby corrected as shown below:

Column 3,
Line 2, reads "case the speed measurement" should read -- speed measurement --.

Signed and Sealed this

Eleventh Day of December, 2001

*Attest:*

NICHOLAS P. GODICI
*Attesting Officer*    *Acting Director of the United States Patent and Trademark Office*